United States Patent

Mohn

[11] Patent Number: 5,479,020
[45] Date of Patent: Dec. 26, 1995

[54] METERING DEVICE FOR A FLUID

[75] Inventor: Frank Mohn, London, England

[73] Assignee: Framo Developments (UK) Limited, London, England

[21] Appl. No.: 240,730

[22] PCT Filed: Nov. 10, 1992

[86] PCT No.: PCT/GB92/02072

§ 371 Date: Jul. 6, 1994

§ 102(e) Date: Jul. 6, 1994

[87] PCT Pub. No.: WO93/10439

PCT Pub. Date: May 27, 1993

[30] Foreign Application Priority Data

Nov. 11, 1991 [GB] United Kingdom ............... 9123937

[51] Int. Cl.$^6$ ............... G01N 23/12; G01F 1/00
[52] U.S. Cl. ............................ 250/356.1
[58] Field of Search ............. 250/356.1; 378/161

[56] References Cited

U.S. PATENT DOCUMENTS

| | | | |
|---|---|---|---|
| 2,953,681 | 9/1960 | Frazier | 250/356.1 |
| 4,862,490 | 8/1989 | Karnezos et al. | 378/161 |
| 5,025,160 | 6/1991 | Watt | 250/356.1 |

FOREIGN PATENT DOCUMENTS

| | | |
|---|---|---|
| 0269432 | 6/1988 | European Pat. Off. . |
| 2069688 | 8/1981 | United Kingdom . |
| 2227118 | 7/1990 | United Kingdom . |

*Primary Examiner*—Carolyn E. Fields
*Attorney, Agent, or Firm*—Young & Thompson

[57] ABSTRACT

A metering device for multiphase fluid, for example, crude oil, comprises a γ or X-ray densitometer incorporating windows for the metering radiation of boron carbide. The boron carbide windows can be provided by a sleeve guiding the fluid flow, the sleeve (51) being reinforced by a thin external layer (52) of carbon fiber embedded in epoxy resin. Alternatively, a steel tube (26) receiving the fluid flow has aligned transverse apertures (47) containing plugs (49) of boron carbide.

11 Claims, 2 Drawing Sheets

METERING DEVICE FOR A FLUID

FIELD OF THE INVENTION

The invention relates to a metering device for a fluid.

BACKGROUND OF THE INVENTION

Particularly in the context of oil extraction systems, it is required to measure the proportions of the components in a multi-phase fluid flow, for example, a crude oil flow containing gas and/or water in varying proportions. It has been proposed in WO 90/13859 (FD20) to provide a mixer apparatus for fluids incorporating a choke or venturi, and to associate measuring or metering equipment with the venturi to determine mass flow rates of the fluid phases flowing through it. Such metering equipment can include a densitometer employing a γ or X-ray source located at one side of the fluid flow for transmitting its radiation transversely through the fluid to a radiation sensor or detector located at the other side of the fluid flow.

The use of a γ or X-ray source and detector presents a problem for such metering equipment in that the tubing within which the fluid flow is confined should be highly transparent to the metering radiation whilst being resistant to the fluid flow and having necessary strength and rigidity. The first of these requirements effectively precludes the use of steel tubing and it has been proposed in EP 0 236 623 to employ beryllium as the material of the wall of the tube across which the radiation is transmitted. The toxicity of beryllium however presents manufacturing problems.

SUMMARY OF THE INVENTION

The present invention accordingly relates to a metering device in which radiation from a source is transmitted through a multiphase or other fluid to be entered to a sensor or detector responsive to the radiation from the source. The invention is concerned with the provision of a device of this kind in which tubing guiding a flowing fluid has appropriate mechanical and physical characteristics and does not unduly attenuate the radiation to be transmitted across it.

The invention accordingly provides a metering device of the kind described in which the material of the tubing wall, or other tubing portion through which the radiation is transmitted, is boron carbide ($B_4C$). Boron carbide has appropriate absorption (or transparency) characteristics for γ or X-rays and is not adversely affected by exposure to such multiphase fluids as are encountered in oil production systems, namely, oil mixed with variable proportions of gas and/or water.

Boron carbide is not however ideal in respect of its mechanical properties. The invention accordingly also provides a metering device of the kind described in which the tubing comprises an inner tube or sleeve of material having high transparency to the radiation, for example, boron carbide, and a reinforcing or supporting outer layer providing additional mechanical strength. The outer layer should of course be as transparent as possible to the radiation. The outer layer can comprise a thread or fiber or other elongate element wound around the sleeve, preferably embedded in a settable plastics material to force a coating of fiber reinforced plastics material. For example, carbon fiber can be wound externally around the boron carbide sleeve to preload the sleeve against the forces it will experience, and the fiber then embedded in the settable plastics material, for example, an epoxy resin. The coating can be employed to bond the inner tube to an external support tube, for example, of steel, provided with apertures, conveniently in the form of aligned radial bores, which can function to collimate the radiation, for the unobstructed transmission of the radiation through it.

The invention also provides a metering device of the kind described in which tubing guiding the fluid flow comprises a tube of material of appropriate mechanical properties, for example, steel, provided with aligned transverse apertures for the radiation, the apertures being closed by elements of material, for example, boron carbide, of relatively high transparency to the radiation. A steel tube can thus be provided with aligned radial bores closed by plugs of boron carbide.

In such arrangements, the tube of steel or the like can function not only as a structural part of the metering device but also as a frame for supporting the radiation source and detector.

BRIEF DESCRIPTION OF THE DRAWINGS

The invention is further described below, by way of example, with reference to the accompanying drawings, in which.

DETAILED DESCRIPTION OF THE INVENTION

Figure 1:
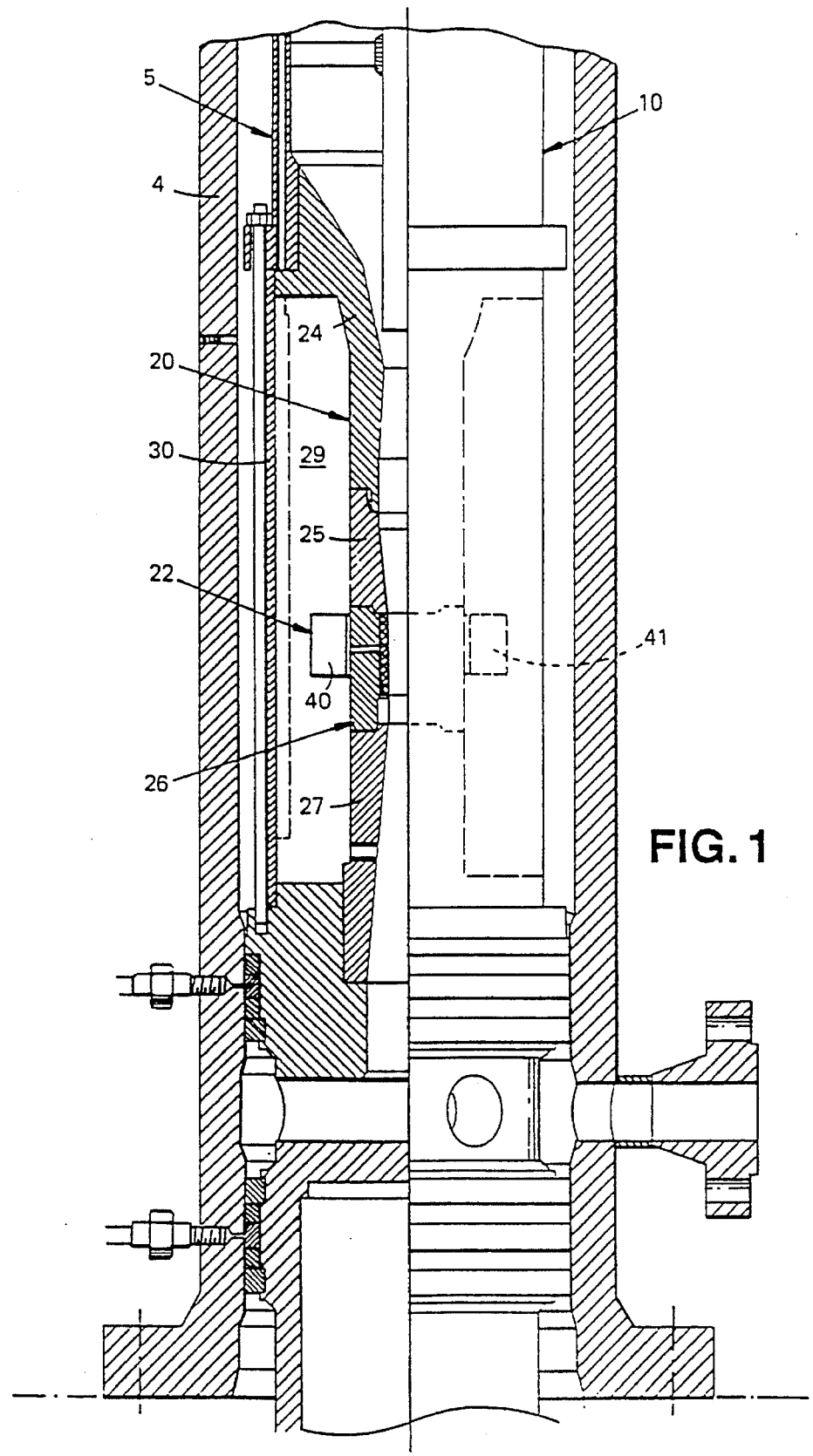
FIG. 1 is a part-sectional side view of part of a subsea installation including a metering device in accordance with the invention located downstream of a mixing unit.

The illustrated installation resembles that shown in FIGS. 4 and 5 of WO 90/13859 (FD20), in that outer tubing 4 forming part of an open-topped receptacle has received therein a cartridge 5 including a mixing unit 10. The mixing unit can correspond functionally to the mixing unit shown in FIG. 2 of WO 90/13859 and has a discharge duct 20 incorporating a venturi, in which the mixing is effected, and which is associated with metering equipment including a gamma or X-ray densitometer 22.

The discharge duct 20 comprises four axially aligned pipe elements 24, 25, 26 & 27 of which the uppermost 24 and the lowermost 27 connect the discharge duct into the cartridge 5. The outer walls of the pipe elements 24–27 are spaced inwardly of adjoining parts of the cartridge to define an annular chamber 29 bounded externally by a sleeve 30, which approximately continues the exterior of the shape of the cartridge.

The upper intermediate pipe element 25 and the lowest element 27 have tapered interiors which guide the fluid flow towards and away from the lower intermediate element 26 which has the least internal diameter, to constitute the actual choke or venturi throat.

Figure 2:
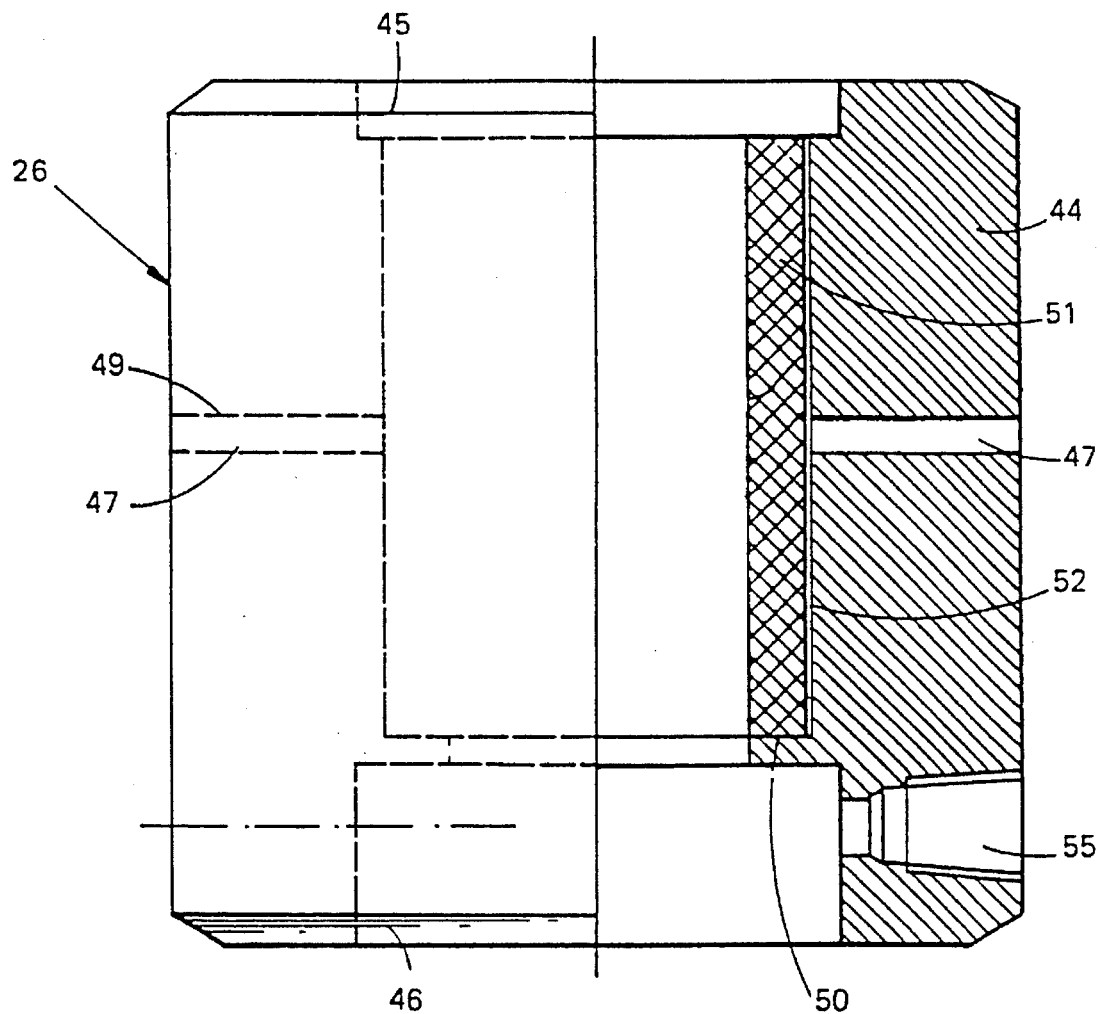
FIG. 2 is a part sectional side view of a pipe element included in the metering device of FIG. 1, shown on a larger scale and illustrating a modification.

The pipe element 26, shown also in FIG. 2, forms part of the γ-ray densitometer 22, which is one of the metering units included in the metering equipment associated with the mixing unit 10. The densitometer comprises a source 40 of gamma radiation diametrically opposed across the element 26 to a sensor or detector 41 capable of detecting the radiation from the source. The source 40 preferably provides radiation at multiple distinct energy levels, or it may comprise multiple sources of radiation at different energy levels. The detector 41 is then capable of distinguishing between radiation at the different energy levels, or comprises multiple detectors responsive to respective energy levels. The detector 41 cooperates with the radiation source 40 to provide output signals dependent on the amount of the radiation absorbed by the different components of multiphase fluid flow in the venturi. The detector output is appropriate by treated in processing equipment (not shown) to provide measures of the mass flow rates of the components of the multiphase fluid flow.

The pipe element 26 comprises an outer sleeve 44, conveniently of steel, of which the external surface is flush with the outer surfaces of the adjoining pipe elements 25 & 27. The interior of the element includes end portions 45 & 46 for receiving interior axially extending locating ring portions of the adjoining pipe elements. Radial bores 47 extend along a diameter through the sleeve to provide passage for radiation from the source 40 through the interior of the element 26 to the detector 41 on the other side. The bores also effect collimation of the radiation.

As shown at the right-hand side of FIG. 2, the interior of the pipe element 25 has a flange 50 near its lower end which supports an inner sleeve 51 of boron carbide of which the inner surface is continuous with those of the flange and of the adjoining pipe elements. The boron carbide inner sleeve 51 requires mechanical reinforcement or support and this is provided by tensioned carbon fiber winding wound around its exterior and embedded in an epoxy resin to form a layer 52, the thickness of which need not be so great as to cause substantial absorption of the radiation.

The radiation source 40 and the detector 41 are mounted on the pipe element 26 within the annular chamber 29 between the tubular elements 24–27 and the sleeve 30 which is filled with an inert gas, for example, nitrogen. The sleeve 30 is preferably counterbalanced externally by a pressure generated between it and the outer tubing 4.

The lower portion of the sleeve 44 is provided with a connection 55 for a pressure sensor included in the metering equipment for supplying to the processing equipment a signal dependent on the pressure drop experienced by the multiphase fluid as it travels through the venturi. A temperature sensor can be included in the metering equipment also.

In a modification, indicated at the left-hand side of FIG. 2, the sleeve 51 is omitted together with the layer 52 and the flowing fluid stream is guided by the interior of the outer steel sleeve 44 directly. The radiation source and the detector are shielded from the fluid by plugs 49 of material, for example boron carbide, of high transparency to the radiation, received in the bores 47. The inner ends of the plugs 49 are preferably flush with the inner wall of the sleeve 44 and shaped accordingly. Although shown as occupying the entire lengths of the bores 47, the plugs 49 preferably extend along only part of the axial length of the bores 47 to limit attenuation of the radiation.

The invention can of course be embodied in a variety of ways other than as specifically described.

I claim:

1. A metering device for metering a flowing fluid, said metering device comprising:

a radiation source for emitting radiation, a sensor responsive to said radiation emitted by said source, pipe means for guiding said flowing fluid, a sleeve of material adapted to transmit said radiation included in said pipe means between said source and said sensor, and mechanical reinforcement means for said sleeve comprising an elongate element wound around said sleeve.

2. The metering device of claim 1, wherein said wound elongate element comprises carbon fiber.

3. The metering device of claim 1 further comprising a settable material, wherein, said wound elongate element is embedded.

4. The metering device of claim 3, wherein said settable material comprises an epoxy resin.

5. The metering device of claim 1 further comprising a rigid pipe member around said wound elongate element, and apertures aligned across said pipe member for transmission of said radiation.

6. The metering device of claim 5 further comprising settable material in which said wound elongate element is embedded, said settable material bonding together said sleeve and said pipe member.

7. The metering device of claim 1, wherein the material of said sleeve is boron carbide.

8. The metering device of claim 1 further comprising tubing around and spaced from said pipe means to define a chamber containing said source and said sensor.

9. The metering device of claim 8, wherein said chamber contains an inert gas.

10. The metering device of claim 1 further comprising a mixing unit having a discharge duct communicating with said pipe means.

11. The metering device of claim 1, wherein said radiation is selected from one of gamma rays and X-rays.

* * * * *